United States Patent [19]

Stahl

[11] Patent Number: 5,464,389
[45] Date of Patent: Nov. 7, 1995

[54] WORKING TIP FOR FRAGMENTING AND ASPIRATING OCULAR TISSUE

[76] Inventor: Norman O. Stahl, 3199 Monterey Dr., Merrick, N.Y. 11566

[21] Appl. No.: 207,374

[22] Filed: Mar. 7, 1994

Related U.S. Application Data

[62] Division of Ser. No. 104,816, Aug. 10, 1993, abandoned.

[51] Int. Cl.⁶ ................................................ A61B 17/20
[52] U.S. Cl. ................................................ 604/22; 606/169
[58] Field of Search ........................... 606/45, 127, 128, 606/167, 169, 170; 128/24 A; 604/19, 22, 27, 35, 48, 272–274, 902

[56] References Cited

U.S. PATENT DOCUMENTS

| | | | |
|---|---|---|---|
| 3,693,613 | 9/1972 | Kelman . | |
| 3,990,452 | 11/1976 | Murry et al. . | |
| 4,169,984 | 10/1979 | Parisi . | |
| 4,465,470 | 8/1984 | Kelman . | |
| 4,496,353 | 1/1985 | Overland et al. | 604/272 |
| 4,504,264 | 3/1985 | Kelman . | |
| 4,531,934 | 7/1985 | Kossovsky et al. . | |
| 4,750,488 | 6/1988 | Wuchinich et al. | 606/128 |
| 4,869,715 | 9/1989 | Sherburne | 604/22 |
| 5,042,461 | 8/1991 | Inoue et al. . | |
| 5,116,343 | 5/1992 | Ams et al. | 606/128 |
| 5,188,102 | 2/1993 | Idemoto et al. | 606/45 X |

*Primary Examiner*—Corrine M. Maglione
*Attorney, Agent, or Firm*—Hoffmann & Baron

[57] ABSTRACT

A method and apparatus are provided for removing tissue, such as cataractous lens tissue, using ultrasonic energy. The apparatus includes a working tip and a transducer or the like for applying ultrasonic vibrations to the working tip. A vacuum source is provided for aspirating fluid through the working tip. The working tip includes a relatively large diameter opening for admitting relatively large tissue fragments. The opening adjoins a bore portion of relatively large diameter. The working tip further includes a bore portion of relatively small diameter and large wall thickness for breaking the tissue fragments into smaller pieces. The method according to the invention includes the steps of moving the end of the working tip into engagement with body tissue, vibrating the tip to cause the body tissue to break into fragments, aspirating fragments into the relatively large diameter portion of the bore, and causing the fragments to pass through the relatively small diameter portion of the bore such that the fragments are efficiently broken into smaller fragments. The end of the working tip may be slotted and the sleeve surrounding the working tip may have a first end portion extending substantially to the end of the working tip and a second end portion terminating well before the end of the tip.

9 Claims, 5 Drawing Sheets

WORKING TIP FOR FRAGMENTING AND ASPIRATING OCULAR TISSUE

This is a divisional of application Ser. No. 08/104,816 filed on Aug. 10, 1993, now abandoned.

BACKGROUND OF THE INVENTION

1. Field of the Invention

The field of the invention relates to surgical instruments for fragmenting and removing tissue from the body, and particularly to the tip or needle portions of such instruments.

2. Brief Description of the Related Art

Instruments for fragmenting and removing tissue through the use of ultrasonic energy are well known in the field of eye surgery. Such instruments include hollow tips which are connected to ultrasonic transducers. The tips are caused to vibrate in a selected manner by the transducers.

The working tip of such a surgical instrument is also frequently connected to a vacuum source. When the tip is moved into engagement with tissue the surgeon wishes to fragment, ultrasonic vibrations are provided to the tip while the vacuum source is actuated. The resulting tissue fragments are accordingly aspirated through the tip. Fluid is provided to the surgical site in order to facilitate the aspiration of tissue fragments and to replace any body fluid which may be lost from the site.

Various working tips have been employed in surgical instruments for fragmenting and aspirating tissue fragments. U.S. Pat. No. 4,504,264 discloses a straight working tip, while U.S. Pat. No. 4,169,984 discloses two working tips, one straight and one curved. The tips disclosed in both patents are formed of thin, titanium tubes.

The working tips of some surgical instruments used in cataract surgery have outside diameters of about one millimeter and longitudinal bores of about 0.8 mm. The walls of such tips accordingly are about 0.1 mm in thickness. Bores of this size provide for the relatively efficient capturing of tissue fragments, but do not transfer ultrasonic energy as well as tips having thicker walls. They also tend to aspirate fluid at a higher rate than the surgeon may desire, making it more difficult to maintain proper pressure within the eye.

Working tips having 0.4 mm bores and wall having thicknesses of 0.3 mm have also been proposed for use in cataract surgery. The thicker walls theoretically provide for more efficient transmission of ultrasonic energy. However, the aspiration of tissue fragments is more difficult as larger fragments may be pushed away by the tip.

A working tip which is said to provide enhanced efficiency of fragmentation and aspiration is disclosed in U.S. Pat. No. 4,531,934. The patented tip is in the form of a needle having a gradually thinning wall between the end at which it is connected to a vibration concentrator and the opposite end through which tissue fragments enter the needle. The needle further includes an end wall which provides a sharp cutting edge where it adjoins the outer wall of the needle.

SUMMARY OF THE INVENTION

It is an object of the invention to provide an apparatus for removal of tissue using ultrasonic energy.

It is another object of the invention to provide a working tip for use in such an apparatus which facilitates the aspiration of tissue fragments while allowing for the efficient transfer of ultrasonic energy.

In accordance with these and other objects of the invention, which will become apparent in the detailed description which follows, an apparatus is provided for fragmenting and aspirating tissue fragments. The apparatus comprises a working tip, means for applying ultrasonic vibrations to the working tip, and means for aspirating fluid through the working tip. The working tip according to a first embodiment of the invention includes an elongate body having a first end which may be adapted for connection to the means for applying ultrasonic vibrations, and a second end. An elongate bore extends through the body between the first and second ends thereof. The bore includes a first portion located between the first and second ends of the body and having a relatively small diameter, and a second portion having a relatively large diameter. The second portion extends between the first portion of the bore and the second end of the body. The first portion of the bore is elongate in order to provide sufficient time and surface area to break-up relatively large tissue fragments. The wall of the elongate body is substantially thicker along the first portion of the bore than the second portion thereof, thereby increasing the efficiency of the tissue fragmentation process.

A method of aspirating and breaking-up tissue fragments is also provided by the invention. The invention includes the steps of providing a working tip including a longitudinal bore having a relatively large diameter portion defining an opening at an end of the tip and an elongate portion of relatively small diameter, moving the end of the tip into engagement with body tissue, vibrating the tip at a sufficient frequency to cause the body tissue to break into fragments, aspirating the fragments into the relatively large diameter portion of the bore, and causing the fragments to pass through the relatively small diameter portion of the bore from the relatively large diameter portion thereof such that the fragments are broken into smaller fragments.

In accordance with a second embodiment of the invention, the working tip of the apparatus is enclosed by a sleeve which is specifically designed for preventing unwanted vibration to tissue adjacent the working tip. Specifically, the sleeve includes an end portion which has a first portion extending substantially to the end of the working tip and an opposing second portion which terminates well before the end of the working tip. The sleeve preferably includes a beveled end portion for providing the desired shielding function.

In accordance with a third embodiment of the invention, a working tip is provided which includes one or more axially extending slots which adjoin the bore of the working tip. Such a construction assists in the efficient transfer of energy from the tip to the surrounding tissue.

In accordance with a fourth embodiment of the invention, the end portion of the working tip is provided with a slot bounded by wall portions extending into the bore thereof. These wall portions assist in breaking up the core of tissue within the bore as the working tip is advanced through body tissue.

DETAILED DESCRIPTION OF THE INVENTION

Figure 1:
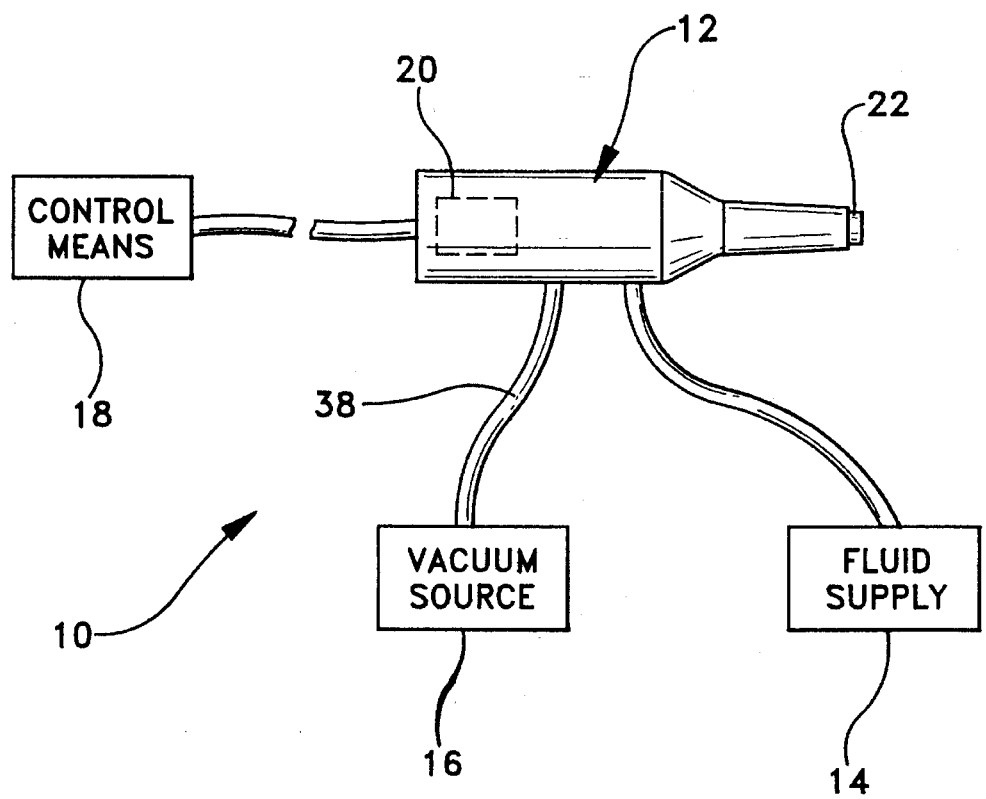
FIG. 1 is a schematic illustration of a system according to the invention.

A system 10 for surgically removing tissue is shown in FIG. 1. The system includes a handpiece 12, a fluid supply 14, a vacuum source 16 and control means 18. The control means may be used for controlling the operation of the handpiece and/or the supply of fluid or vacuum pressure to the handpiece in a well known manner. The vacuum source may be in the form of a suction pump, while the fluid supply may be a fluid container for supplying fluid under the force of gravity, a peristaltic pump, or other suitable apparatus.

Figure 3:
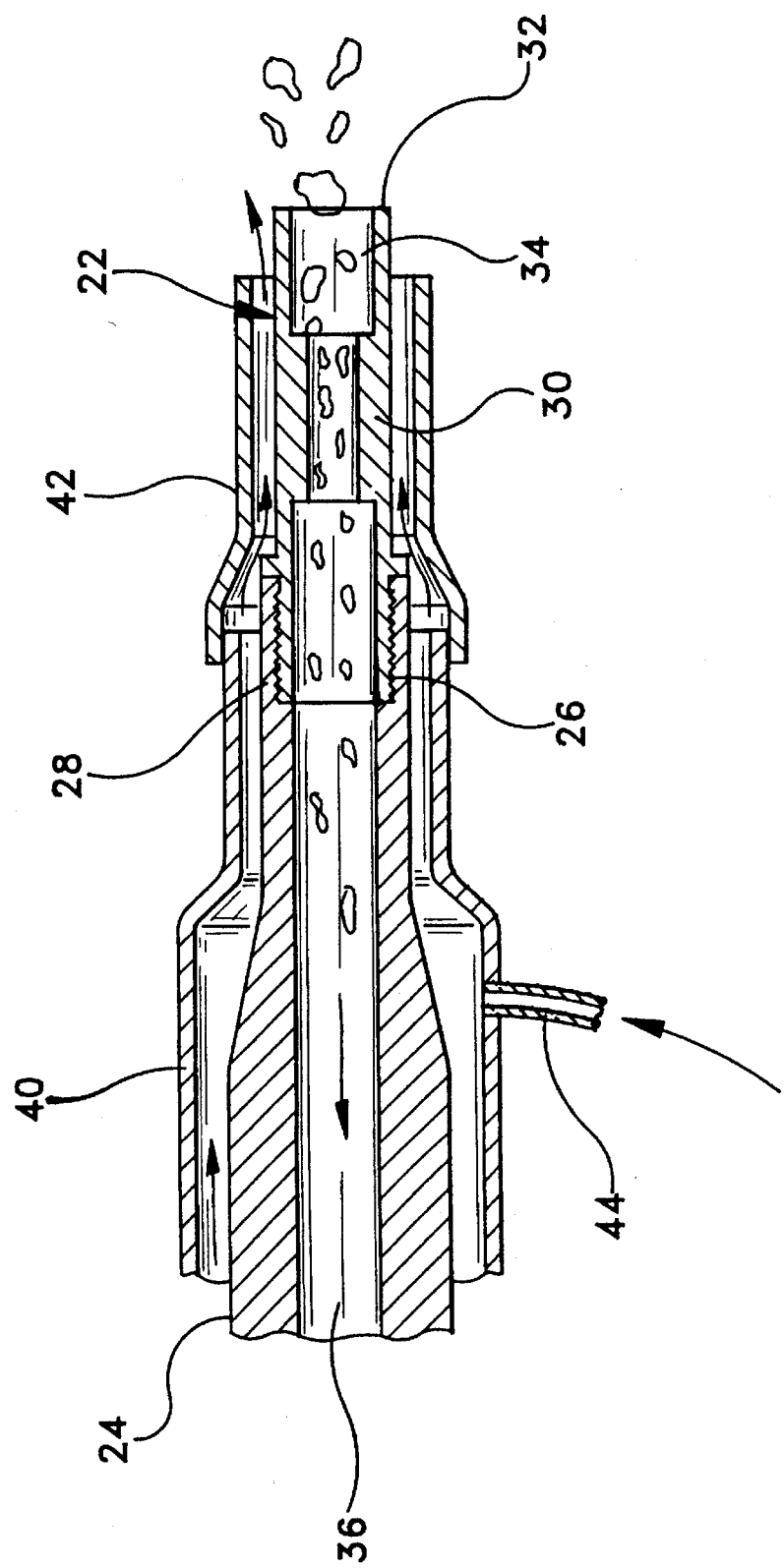
FIG. 3 is an enlarged, sectional view of the front portion of a handpiece according to the invention.

The handpiece 12 includes an ultrasonic transducer 20 for causing the vibration of a working tip 22. The power supply (not shown) for the transducer may be incorporated within the control means 18. As shown in FIG. 3, a connecting member 24 may be provided for connecting the working tip 22 to the transducer. (Alternatively, as disclosed in U.S. Pat. No. 4,169,984, the tip may extend through the transducer). The working tip includes an externally threaded first end 26 which is removably coupled to the internally threaded end 28 of the connecting member.

Figure 2:
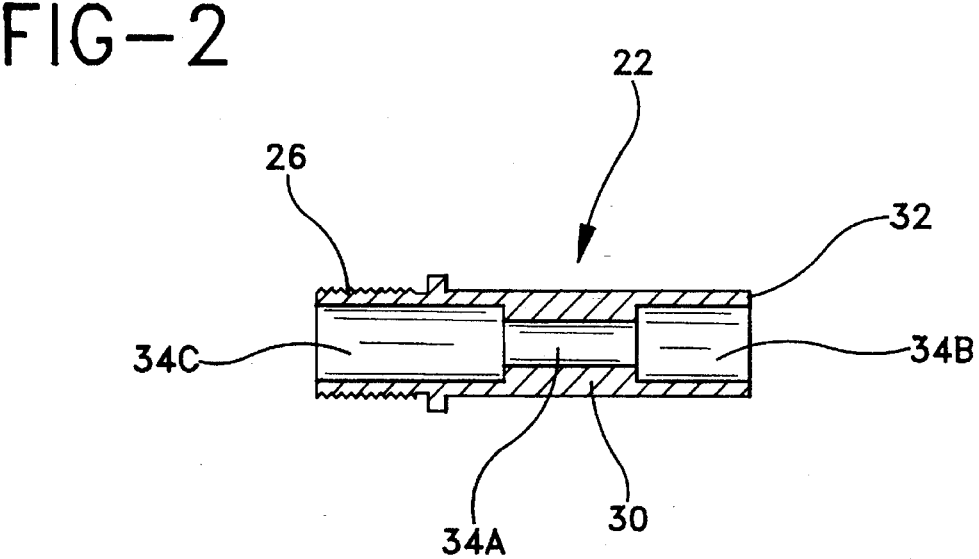
FIG. 2 is an enlarged, sectional view of a working tip according to the invention.

Referring to FIGS. 2 and 3, the working tip 22 includes an elongate body 30 which is preferably made from titanium. The body is substantially cylindrical, and has a substantially uniform outside diameter of about one millimeter. The particular working tip disclosed herein is accordingly suitable for use in cataract surgery. Tips of different dimensions may be usable in different types of surgery. As discussed above, the working tip may include an obtuse angle therein depending upon the needs of the surgeon.

The tip 22 includes a second end 32 for engaging cataractous lens tissue. While shown as a blunt end in the drawings, it is well known to employ a beveled end for placement against such tissue. A longitudinal bore 34 extends through the entire working tip. The bore 34 is in fluid communication with a bore 36 extending through the connecting member 24. A first tube 38 is provided for establishing fluid communication between the bore 36 and the vacuum source 16.

The longitudinal bore 34 extending through the working tip 22 includes three discrete portions. A first elongate portion 34A thereof is located between the first and second ends of the working tip. The length of this portion is preferably between about 1.5–2.5 mm. A second portion 34B extends from the first portion to the second end 32 of the tip. A third portion 34C of the bore 34 extends between the first portion 34A and the threaded end 28 of the tip. All three bore portions are substantially coaxial. The thickness of the wall defining the tip body 30 is substantially greater along the first portion 34A of the bore than along the second portion 34B thereof. In a preferred embodiment of the invention, the wall thickness along the first portion 34A is about 0.25 mm. In contrast, the wall thickness along the second portion 34B is about 0.1 mm. The second portion 34B of the bore accordingly has a diameter of about 0.8 mm, which allows relatively large tissue fragments to enter the working tip. This portion 34B preferably has a length of about two millimeters. Once drawn therein, the fragments are further broken up into smaller pieces. The smaller diameter portion of the bore, being about 0.5 mm, enhances the efficiency of the fragmentation procedure as the tissue fragments pass through the tip. Chatter, which is caused by the fragments repeatedly engaging the wall as they pass through a large bore, is also likely to be reduced.

As the system 10 causes removal of tissue fragments and fluid from the surgical site, it is necessary to replenish the site with fluid in order to maintain proper pressure within the eye. The handpiece 12 accordingly includes a casing 40 having a sleeve 42 mounted thereto for receiving fluid from the supply 14. Irrigation fluid is provided through a tube 44 connected between the fluid supply 14 and casing 40. The fluid travels through the space between the working tip 22 and sleeve 42, and exits from the front end of the handpiece as shown in FIG. 3. Alternatively, irrigation fluid may be provided to the surgical site independently of the handpiece.

The operation of the system, and particularly the working tip according to the present invention, shall now be described with respect to cataract surgery. The tip is introduced into the anterior chamber of the eye through a small incision. Once so introduced, the end 32 of the tip engages the cataractous tissue, causing the tissue to fragment as the tip is subjected to ultrasonic vibrations. Tissue fragments and fluid are aspirated through the working tip while irrigation fluid is supplied through the annular channel surrounding the tip. Relatively large tissue fragments are able to enter the working tip due to the large opening at the front end 32 thereof. The front portion 34B of the bore, being elongate and having a relatively large diameter, facilitates the capture of such fragments. Once captured, the fragments must then pass through the relatively small diameter portion 34A of the bore.

The first portion 34A of the bore 34 is designed such that the wall of the working tip adjoining this portion will cause the fragments to be broken into even smaller fragments. The fragments are more likely to engage the vibrating wall due to the small diameter of the bore. As the first portion 34A of the bore is elongate, the fragments are subjected to considerable pulverizing action as they pass therethrough. They are accordingly reduced in size by the time they enter the third portion 34C of the bore and pass from the working tip 22.

The small bore portion 34A of the working tip not only increases the efficiency of breaking up the fragments passing therethrough, but also causes fluid to be aspirated from the eye at a slower rate as compared with most conventional working tips of uniform diameter. It is accordingly easier for the surgeon to maintain proper pressure within the eye than where fluid is aspirated at a relatively high rate.

Figure 4:
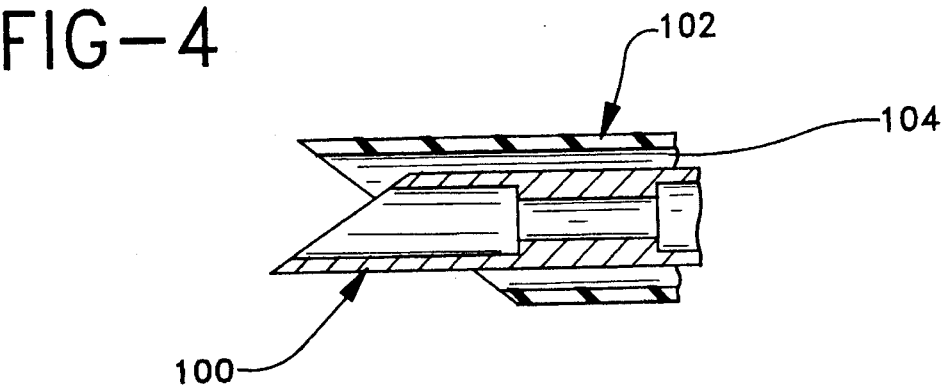
FIG. 4 is a sectional view of a needle/sleeve assembly in accordance with an alternative embodiment of the invention.

Referring now to FIG. 4, an alternative embodiment of the invention is disclosed wherein the titanium working tip 100 has a bevelled end and the sleeve 102 encasing the working also has a bevelled end. The structure of the assembly may otherwise by substantially the same as that shown in FIGS. 1 and 3. The sleeve 102 is preferably made from a material such as silicon, and is secured to the casing of the handpiece by threads or other appropriate attachment means. Irrigation fluid is provided through the annular passage 104 defined between the working tip 100 and the sleeve.

An additional function of the sleeve is to restrict the transmission of ultrasonic energy to those areas where the surgeon desires to fragmentize body tissue. By providing a sleeve having one portion which extends further axially than the other, the ultrasonic vibrations are confined to a more restricted area than if the end of the sleeve were blunt. If the tip end is bevelled as shown, the bevel of the sleeve is preferably oriented about 180° from the direction of the bevel of the needle. While a bevelled sleeve is preferred for purposes of fabrication, the end of the sleeve may have other configurations designed to provide greater shielding about one portion of the working tip than another.

Figure 5:
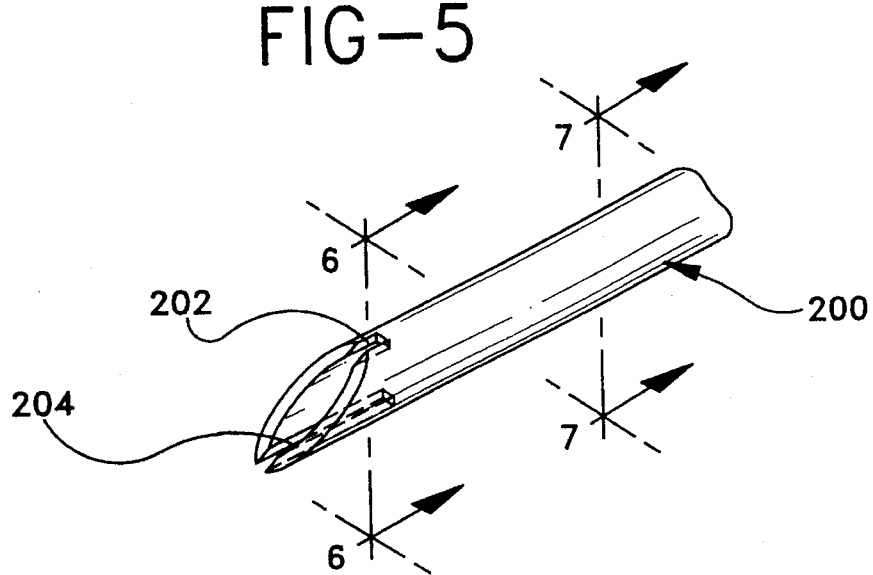
FIG. 5 is a top perspective view of a needle according to another embodiment of the invention.
Figure 6:
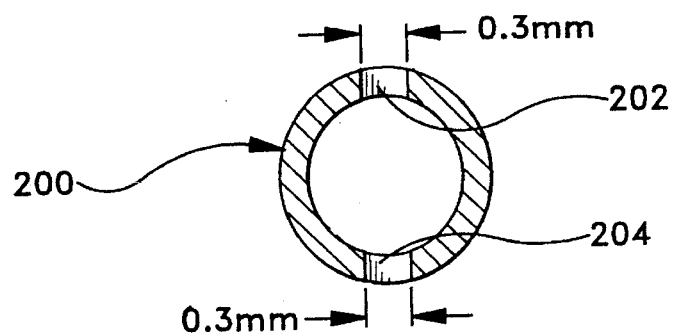
FIG. 6 is a sectional view taken along line 6—6 of FIG. 5.
Figure 7:
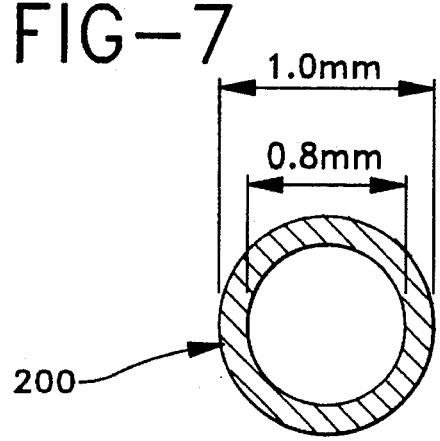
FIG. 7 is a sectional view taken along line 7—7 of FIG. 5.

FIGS. 5–7 show an alternative embodiment of the invention wherein the working tip 200 includes a bevelled end and a pair of slots 202, 204 extending substantially parallel to the longitudinal axis of the tip. Like the other working tips described above, the outside diameter is preferably about 1.0 mm for use in eye surgery. One slot 202 is about 0.5 mm is length while the other has a length of about 1.5 mm. The dimensions can vary depending upon the size if the working tip. The width of each slot is about 0.3 mm in the embodiment shown in FIG. 5. If a single slot is employed, the width would preferably be about 0.3–0.5 mm.

The slot(s) in the end of the working tip provide a more efficient transfer of sonic energy to the body tissue than unslotted tips. The increased area of the free border of the tip contributes to this efficiency. A slot bounded by parallel side walls is shown in the Figures, and can be fabricated by a process such as milling. Slots of other configurations are contemplated by the invention.

Figure 8:
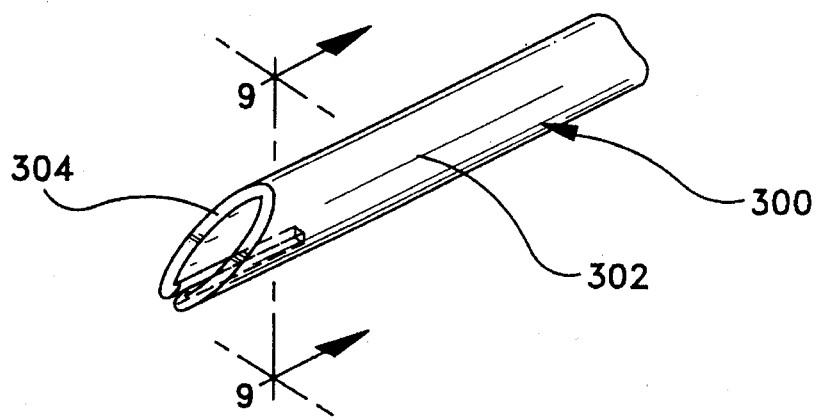
FIG. 8 is a top perspective view of a needle according to another embodiment of the invention.
Figure 9:
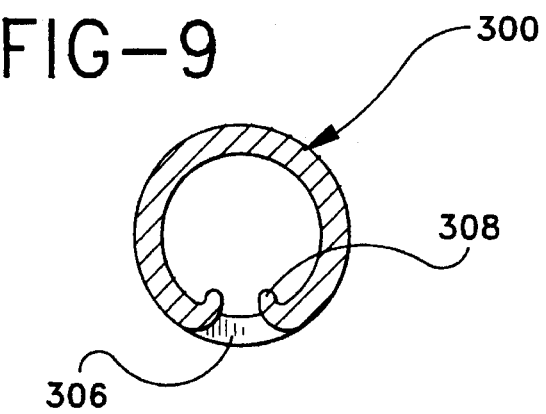
FIG. 9 is a sectional view taken along line 9—9 of FIG. 8.

FIGS. 8–9 illustrate another embodiment of the invention similar to that shown in FIGS. 5–7, but including only a single slot. The working tip 300 includes a cylindrical body 302 having a bevelled end 304. A slot 306 having a length of about 1.5 mm and a width between about 0.3–0.5 mm is provided in the end portion of the body which opposes the bevelled surface. Unlike the slots employed in the working tip 200 shown in FIG. 5, portions 308 of the wall extend within the bore of the tip, as best shown in FIG. 9. These wall portions help break up the core of tissue within the bore as the working tip is vibrated and passed through body tissue.

All of the embodiments of the invention shown in FIGS. 4–9 are usable in the apparatus shown in FIG. 3 in place of the working tip 22 and/or sleeve 42 shown therein. Illustration of these embodiments as incorporated in such an apparatus is unnecessary as the remaining components of the apparatus would not require change. The sleeve shown in FIG. 4 would be usable in conjunction with any of the working tips disclosed herein, and should not be considered as restricted to use with the tip shown in this figure.

Figure 10:
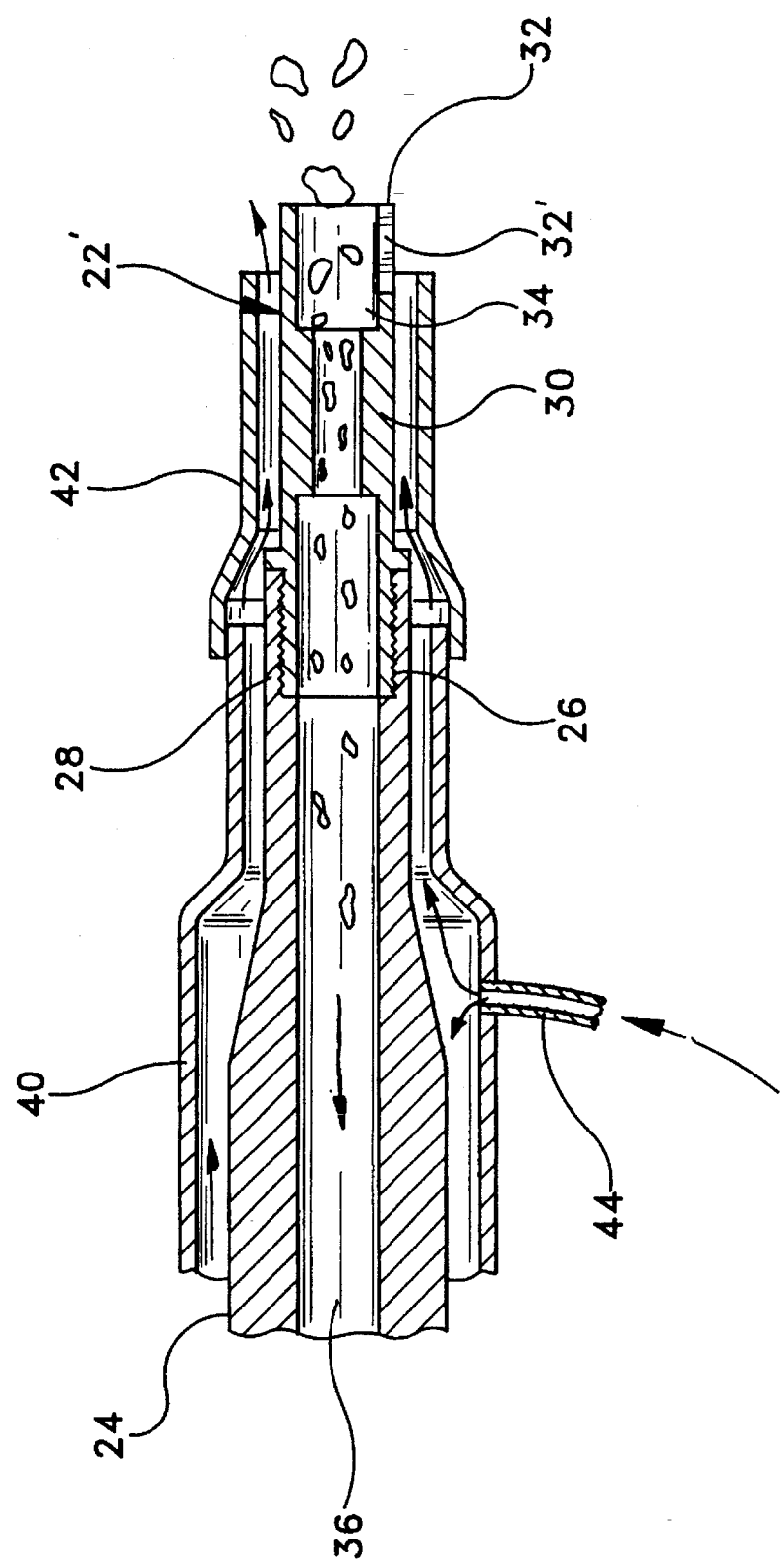
FIG. 10 is an enlarged, sectional view of the front portion of a handpiece including a working tip in accordance with another embodiment of the invention.

FIG. 10 shows an embodiment of the invention which is identical to that shown in FIG. 3 with the exception of the working tip 22' which, in this embodiment, includes an elongated slot 32' extending from the second end 32 thereof.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A working tip for fragmenting and aspirating ocular tissue, comprising:

an elongate body including a generally cylindrical wall having a substantially uniform outside diameter of about one millimeter and an elongate bore extending therethrough, said bore including a first elongate portion having a relatively small diameter, a second elongate portion having a relatively large diameter, said second elongate portion defining an opening for admitting tissue fragments into said bore, said wall being substantially thicker along said first elongate portion of said bore than said second elongate portion, and a third elongate bore portion having a relatively large diameter, said third elongate bore portion adjoining said first elongate bore portion and defining a second opening in said body through which tissue fragments are removed from said bore, said first elongate portion providing fluid communication between said second and third elongate portions, and wherein said elongate body includes an end portion and an end face, and a slot extending through said cylindrical wall at said end portion and end face.

2. An apparatus for fragmenting ocular tissue, comprising:

a working tip including an elongate body having generally cylindrical wall defining a longitudinal bore extending therethrough, a first end including an opening for admitting tissue fragments into said bore, an elongate, longitudinally extending first slot extending through said cylindrical wall and adjoining said bore and said opening, said first slot extending substantially parallel to the longitudinal axis of said bore, said cylindrical wall defining a free border bounding said first slot, and a second slot extending through said cylindrical wall in opposing relation to said first slot;

means for applying ultrasonic vibrations to said working tip, and means for aspirating fluid through said working tip.

3. An apparatus as described in claim 2, wherein said first end of said elongate body is bevelled, and said first slot has a length exceeding the length of the second slot.

4. An apparatus as described in claim 3, wherein said first slot is about three times longer than said second slot.

5. An apparatus as described in claim 2, including an elongate sleeve, said working tip being positioned substantially entirely within said sleeve, said first end of said working tip extending outside said sleeve.

6. An apparatus as described in claim 5, wherein said sleeve includes a bevelled end, and said first end of said working tip is bevelled.

7. A working tip for fragmenting and aspirating ocular tissue, comprising:

an elongate body including a generally cylindrical wall having an outside diameter sufficiently small for entering an incision made within an eye for surgical purposes, a longitudinal bore extending through said elongate body, a first end including an opening for admitting tissue fragments into said bore, and a slot extending through said cylindrical wall, said slot adjoining said bore and said opening, said cylindrical wall defining a free border bounding said slot, and at least one projection extending radially inwardly into said bore from said cylindrical wall.

8. A working tip as described in claim 7 wherein said slot is bounded by a pair of substantially parallel, opposing surfaces of said cylindrical wall, said slot having an elongate configuration.

9. A working tip as described in claim 7 including a pair of opposing projections extending into said bore from said cylindrical wall, said projections adjoining said slot.

* * * * *